(12) United States Patent
Kaandorp et al.

(10) Patent No.: US 10,518,102 B2
(45) Date of Patent: Dec. 31, 2019

(54) BODY ILLUMINATION DEVICE

(71) Applicant: KONINKLIJKE PHILIPS N.V., Eindhoven (NL)

(72) Inventors: Wouter Petrus Kaandorp, Best (NL); Rob Gerard Wijnand Maria Maessen, Mariaheide (NL)

(73) Assignee: Koninklijke Philips N.V., Eindhoven (NL)

( * ) Notice: Subject to any disclaimer, the term of this patent is extended or adjusted under 35 U.S.C. 154(b) by 371 days.

(21) Appl. No.: 15/125,609

(22) PCT Filed: Mar. 23, 2015

(86) PCT No.: PCT/EP2015/056029
§ 371 (c)(1),
(2) Date: Sep. 13, 2016

(87) PCT Pub. No.: WO2015/150126
PCT Pub. Date: Oct. 8, 2015

(65) Prior Publication Data
US 2017/0007844 A1  Jan. 12, 2017

(30) Foreign Application Priority Data

Apr. 2, 2014  (EP) .................................... 14163117

(51) Int. Cl.
*A61N 5/06* (2006.01)
*A61N 5/00* (2006.01)

(52) U.S. Cl.
CPC ...... *A61N 5/0616* (2013.01); *A61N 2005/007* (2013.01); *A61N 2005/064* (2013.01);
(Continued)

(58) Field of Classification Search
CPC ............ A61N 5/0616; A61N 2005/007; A61N 2005/064; A61N 2005/0645; A61N 2005/0665
(Continued)

(56) References Cited

U.S. PATENT DOCUMENTS 6,119,474 A * 9/2000 Augustine ............ A47G 9/0215
607/107
6,443,978 B1 * 9/2002 Zharov ................ A61N 5/0616
606/13
(Continued)

FOREIGN PATENT DOCUMENTS

DE  202012004264 U1  7/2013
FR       2794373 A1  12/2000
(Continued)

*Primary Examiner* — Kennedy Schaetzle

(57) ABSTRACT

A body illumination device adapted to surround at least a part of a user including at least one inflatable structural element and a light emitter. The at least one inflatable structural element includes a first inflatable structural element including a first inflatable chamber including a first wall and a second wall which is transparent to the light emitted by the light emitter such that light can be is provided to the user from the light emitter through the second wall. The light emitter is on or integrally formed with said first wall and is for providing light to the user. The body illumination device may be stored easily in a deflated state and may be used in the treatment of psoriasis, eczema or skin cancer.

15 Claims, 4 Drawing Sheets

(52) U.S. Cl.
CPC ................ *A61N 2005/0645* (2013.01); *A61N 2005/0665* (2013.01)

(58) Field of Classification Search
USPC ............................................... 607/80, 88–94
See application file for complete search history.

(56) References Cited

U.S. PATENT DOCUMENTS

| | | | |
|---|---|---|---|
| 6,596,016 | B1 | 7/2003 | Vreman et al. |
| 7,022,130 | B2 | 4/2006 | Gammons et al. |
| 7,994,489 | B2 | 8/2011 | Fiset |
| 8,886,334 | B2* | 11/2014 | Ghaffari ............. A61B 1/00082 607/115 |
| 2002/0026226 | A1* | 2/2002 | Ein ........................ A61F 7/007 607/108 |
| 2005/0277837 | A1* | 12/2005 | Coulston ............ A41D 13/1281 600/499 |
| 2009/0000614 | A1 | 1/2009 | Carrano |
| 2009/0217598 | A1 | 9/2009 | Schlereth |
| 2010/0121420 | A1* | 5/2010 | Fiset ........................ A61N 5/06 607/94 |
| 2012/0065709 | A1* | 3/2012 | Dunning ................. A61N 5/06 607/88 |
| 2012/0165759 | A1* | 6/2012 | Rogers ................ A61B 5/6867 604/264 |
| 2012/0253433 | A1* | 10/2012 | Rosen .................. A61N 5/0621 607/91 |
| 2013/0068851 | A1 | 3/2013 | Young |
| 2013/0123621 | A1 | 5/2013 | Sham et al. |
| 2013/0281815 | A1* | 10/2013 | Varadan ............. A61B 5/04085 600/388 |

FOREIGN PATENT DOCUMENTS

| | | |
|---|---|---|
| JP | 2011078472 A | 4/2011 |
| WO | 2007021948 A2 | 2/2007 |

* cited by examiner

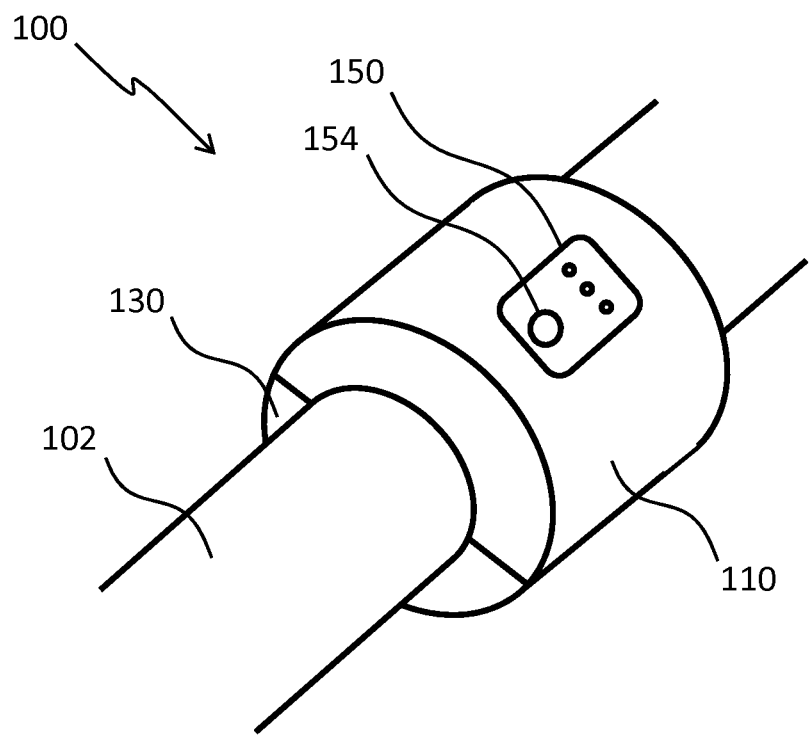
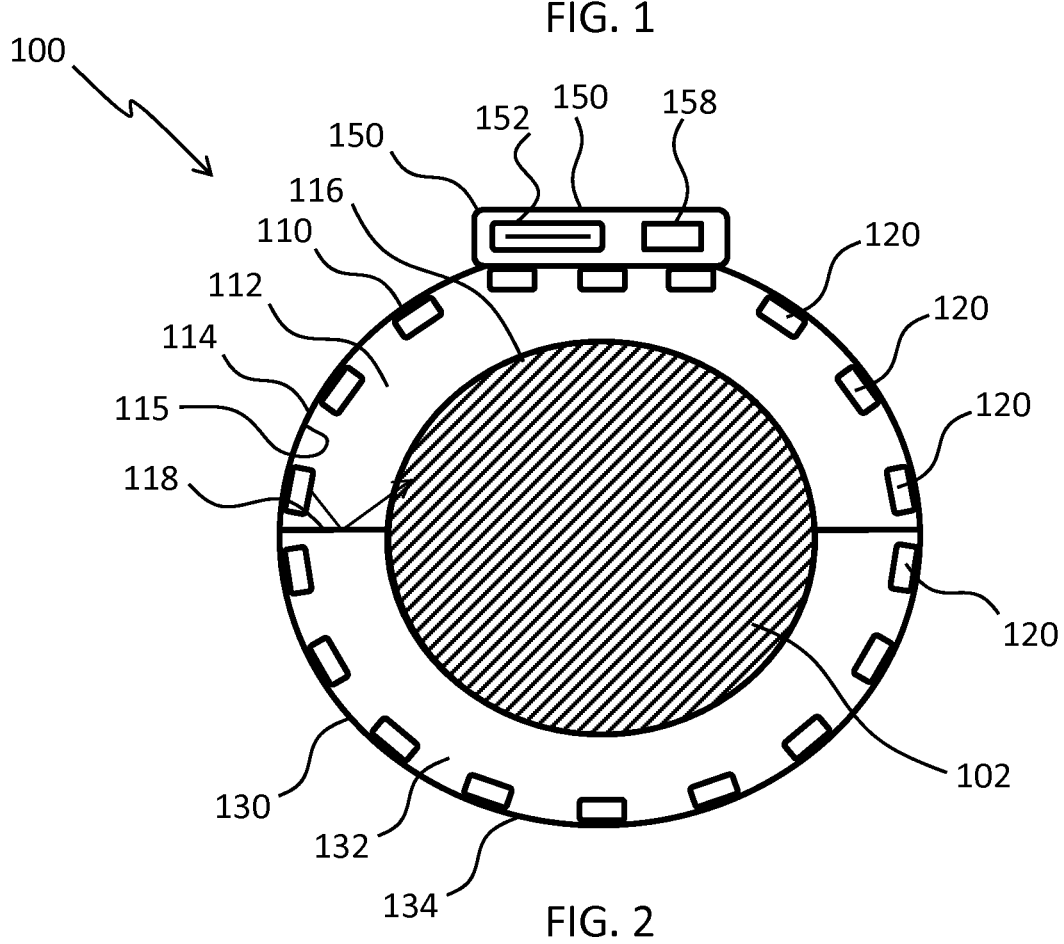

BODY ILLUMINATION DEVICE

CROSS-REFERENCE TO PRIOR APPLICATIONS

This application is the U.S. National Phase application under 35 U.S.C. § 371 of International Application No. PCT/EP2015/056029, filed on Mar. 23, 2015, which claims the benefit of European Patent Application No. 14163117.6, filed on Apr. 2, 2014. These applications are hereby incorporated by reference herein.

FIELD OF THE INVENTION

This invention relates to a body illumination device, for providing light to a living body.

BACKGROUND OF THE INVENTION

The invention is of particular interest for devices which enable light treatment therapy. For the treatment of the skin with light, e.g. the treatment of Psoriasis Vulgaris eczema, or skin cancer, various devices are known. These devices may be difficult to store, difficult to use and/or relatively expensive.

It would be advantageous to provide a body illumination device which is easy to store and use, and relatively cost-effective.

SUMMARY OF THE INVENTION

The invention is defined by the claims.

According to the invention, there is provided a body illumination device adapted to surround at least a part of a user. The body illumination device comprises at least one inflatable structural element including a first inflatable structural element comprising a first inflatable chamber comprising a first wall, a light emitter on or integrally formed with said first wall for providing light such as treatment light to the user, and a second wall which is transparent to the light emitted by the light emitter such that light can be provided to the user through the second wall.

This body illumination device may be stored easily in a deflated state. Further, this body illumination device does not require relatively expensive structural components, such that it may be provided in a cost-effective manner. Additionally, the device may be easy to use.

The body illumination device may be adapted to surround at least one of, a limb, the torso, the neck or the head of the user.

Such a device may be relatively comfortable for the user, in particular, pinch points which may be provided by prior art body illumination devices may be avoided. Further, when deflated there may be a large clearance between the device and the user such that the device can be conveniently and comfortably positioned on the user. This may be particularly important where the skin of the user is damaged, for example by Psoriasis. Further, this device may be provided in a one-size-fits-all format (which can provide simplicity), the device may be integral, the device may be relatively cost effective, and consumer purchasing decisions may be made easier. Accordingly, such a device may be particularly suitable for home therapy.

In use, the limb, the torso, the neck or the head of the user may be surrounded by the at least one inflatable structural element.

Alternatively, the body illumination device may be adapted to surround the user. For example, the body illumination device may be adapted to form a cabin into which the user can stand and/or lay down. Such a device may be easy to install and relatively light weight in comparison with prior art body illumination devices which can surround a user.

The light emitter may be provided in the base of the first inflatable structural element. Such an arrangement may be advantageous as it may not be necessary for the first inflatable structural element to support the weight of the light emitter.

The first inflatable structural element may further comprise a second wall which is transparent to the light such that light can be provided to the user through the second wall and the light emitter may be on the internal surface of the first wall or integrally formed with the first wall.

The first wall may face the second wall. This can enable light to travel efficiently from the light emitter to the skin of the user.

The first inflatable structural element may further comprise reflectors and/or diffusers for reflecting and/or diffusing the light such that the light so reflected and/or diffused can be provided to the user through the second wall.

This may provide a device having a great luminous efficiency and/or a more even distribution of light output.

The body illumination device may further comprise an air pump for inflating the at least one inflatable structural element. This can enable easy inflation of the at least one inflatable structural element.

The at least one inflatable structural element may comprise an exhaust arranged to cool the user in use. This can provide a more comfortable experience for the user.

The light emitter may comprise a solid state lighting element. In particular, the light emitter may comprise a LED.

The solid state lighting element may be integrally formed with the first wall of the first inflatable structural element. This can provide a device with a smooth profile in its storage or mounting configuration.

The at least one inflatable structural element may further comprise a second inflatable structural element for providing a thermal cushion between the user and the light emitter. The second inflatable structural element is at least partially transparent to the light. This can provide a more comfortable experience for the user as the thermal cushion can reduce the amount of heat from the light emitter reaching the user.

The body illumination device may further comprise a controller which comprises a user interface and driver circuitry for driving the light emitter.

There is also provided a method of treatment comprising providing treatment light to the user using a device as provided above.

Accordingly, the body illumination device provided above is for use in a method of treatment comprising the steps of:
  surrounding at least part of a user,
  inflating at least one inflatable structural element,
  providing power to a light emitter, and
  providing treatment light to the user.

The treatment may for example be of psoriasis, eczema, or skin cancer.

BRIEF DESCRIPTION OF THE DRAWINGS

Examples of the invention will now be described in detail with reference to the accompanying drawings, in which:

FIG. 1 shows a schematic perspective view of a body illumination device in use on a limb of a user;

FIG. 2 shows a schematic cross-sectional of the body illumination device of FIG. 1, also in use;

DETAILED DESCRIPTION OF THE EMBODIMENTS

The invention provides a body illumination device adapted to surround at least a part of a user and which comprises at least one inflatable structural element and a light emitter. The at least one inflatable structural element includes a first inflatable structural element. The first inflatable structural element comprises a first inflatable chamber comprising a first wall. The light emitter is on or integrally formed with said first wall and is for providing light to the user, for example for implementing a light therapy.

Figure 3:
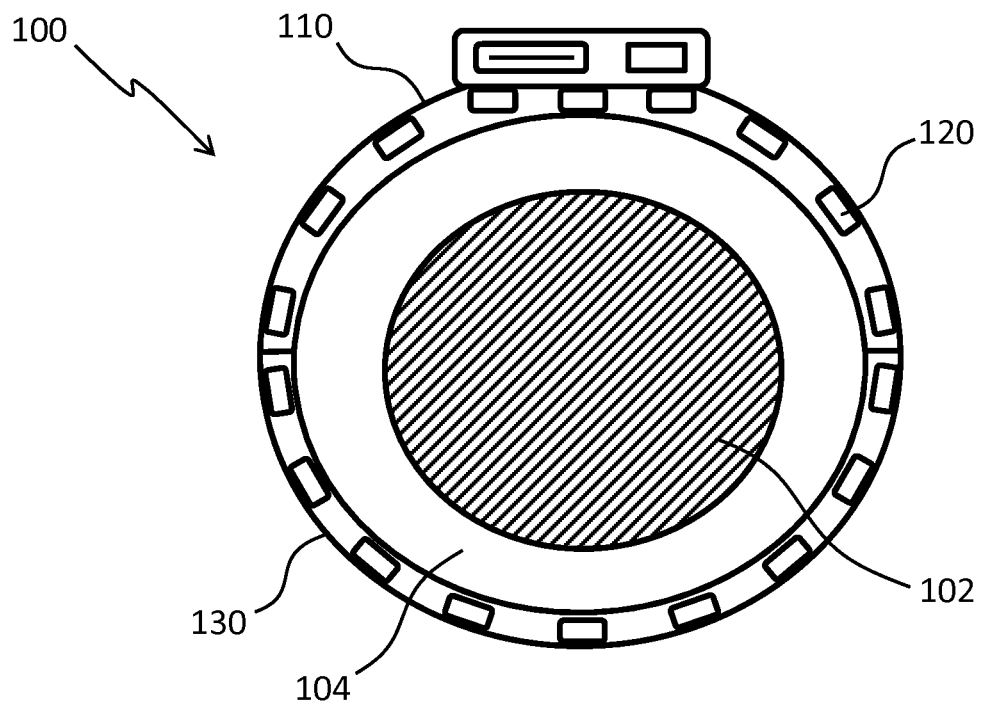
FIG. 3 shows a schematic cross-sectional view of the body illumination device of FIG. 1 in a deflated state.

FIGS. 1 to 3 show a body illumination device, indicated generally at 100. The body illumination device 100 is adapted to surround at least a part of a user 102. The body illumination device 100 comprises at least one inflatable structural element including a first inflatable structural element 110. As shown in FIG. 2, the first inflatable structural element 100 comprises a first inflatable chamber 112 comprising a first wall 114. The body illumination device 100 also comprises a light emitter 120 on said first wall 114 for providing light to the user 102. Alternatively, the light emitter 120 may be integrally formed with the first wall 114. Thus, there is at least one inflatable element which includes a light emitter.

The use of an inflatable structure has various advantages. As will be apparent from the description below, different advantages are obtained from different designs. Some designs enable the structure to be inflated around an area of the user so that the structure adapts itself to the size and shape of that area of the user, so enabling a single design to be used for different patient sizes. Some larger designs enable the structure to be deflated for easier storage.

In particular, when the body illumination device 100 is not in use the at least one inflatable structural element may be deflated, this may provide a compact body illumination device 100, which therefore may be stored easily.

Further, this body illumination device 100 does not require relatively expensive structural components, such that the body illumination device 100 may be provided in a cost-effective manner.

Additionally, the body illumination device 100 may be easy to use, as the device 100 may be used by simply inflating the at least one inflatable structural element and switching on the light emitter 120 to provide light to the user 102.

The body illumination device 100 may comprise a plurality of light emitters 120, as illustrated in the Figures. The plurality of light emitters may be arranged to form an array. Below, only one light emitter 120 is discussed, however, it should be understood that unless the context requires otherwise, characteristics of the light emitter 120 may apply to some or all of the plurality of light emitters, if present.

As illustrated in FIGS. 1 to 3, the at least one inflatable structural element may include a further inflatable structural element 130. Thus, the structure may have one or more inflatable compartments, and one or more of these compartments may be provided with the light emitter. FIG. 2 shows a design with two compartments. The further inflatable structural element 130 may be similar or identical to the first inflatable structural element 110 and comprise a first inflatable chamber 132 comprising a first wall 134. A light emitter 120 may be on or integrally formed with said first wall 134 for providing light to the user 102. The further inflatable structural element 130 may be in fluid communication with the first inflatable structural element 110 such that inflation of one inflatable structural element causes inflation of the other. Alternatively, the further inflatable structural element 130 may be provided with its own individual air supply. This compartmented structured has improved rigidity, for example.

FIGS. 1 to 3 show the body illumination device 100 around a limb of the user 102. Indeed, the body illumination device 100 illustrated in FIGS. 1 to 3 is adapted to surround a limb of the user. Specifically, the at least one inflatable structural element may be sized so as to receive an arm or a leg in use. By inflating the structure, a contact fit around the limb is provided, so that the structure adapts itself to the size of the limb.

This can also provide a body illumination device 100 which is relatively comfortable for the user 102, specifically, the at least one inflatable structural element can provide an even pressure on the user 102, which can be more comfortable than prior art adjustable means for fixing a body illumination device to a user. In particular, pinch points which may be provided by prior art body illumination devices may be eliminated.

Further, as illustrated in FIG. 3, when the at least one inflatable structural element is deflated there is a large clearance 104 between the body illumination device 100 and the limb of the user 102. This can enable the device 100 to be conveniently and comfortably positioned and fixed on the user 102. A large clearance 104 between the body illumination device 100 and the user 102 may be particularly advantageous for users having damaged skin, for example skin damaged by Psoriasis. In particular, damaged skin may be particularly sensitive to friction caused by the positioning of a close fitting prior art body illumination device. The body illumination device 100 may be positioned in its deflated state illustrated in FIG. 3 and then inflated in position (as illustrated in FIGS. 1 and 2) in order to position the device 100 in place with little or no friction between the skin of the user 102 and the device 100. Accordingly, the device 100 may be easily mounted on the user 102 and may even provide a superior treatment, as use of the device 100 can cause less friction damage to the potentially sensitive skin of the user 102.

Additionally, use of at least one inflatable structural element makes it feasible to provide a body illumination device 100 in a one-size-fits-all format. Specifically, prior art body illumination devices are provided in a relatively large number of formats in order to provide body illumination devices which can be used in different bodily locations. For example, the prior art provides a first body illumination device for treating a thigh and a different second body illumination device for treating a forearm. To avoid this need to provide completely different devices, it is known from the prior art to provide a separate body illumination device and a further separate fixation device for fixing the body illumination device to a user. In this way, only different fixation devices are required and not different body illumination devices. However, this still requires the provision of different sizes of fixation device. Due to the flexibility which can be afforded by use of the at least one inflatable structural element, the body illumination device 100 may be sized such that it can be used to treat both a thigh and a forearm of the user 102.

The provision of a one-size-fits-all format can provide additional advantages over and above simplicity. For example, if the device is a one-size-fits-all the device may be used for a variety of different treatments. Specifically, as the body illumination device 100 may be used in a number of different bodily locations it is not necessary to provide separate fixation and treatment devices. As fewer differently sized devices 100 are necessary to provide body illumination devices which can be used in a range of bodily locations, the number of sizes of devices which it is necessary for a manufacturer to provide is reduced. This may provide greater economies of scale and can hence enable the body illumination device 100 to be provided more cost-effectively.

Additionally, the provision of a one-size-fits-all format can make consumer purchasing decisions easier, as it is necessary for the consumer to discriminate between fewer different body illumination devices 100. Therefore, such a body illumination device 100 may be particularly suitable for home therapy.

If the device 100 is adapted to surround at least one of, a limb, the torso, the neck or the head of the user 102 then the at least one inflatable structural element may surround the limb, the torso, the neck or the head of the user 102 in use. For example, as illustrated in FIGS. 1 to 3, the limb is surrounded by the first inflatable structural element 110 and the further inflatable structural element 130. The inflating of the structure thus provides the required fixation to the user and accommodates different user sizes.

As shown in FIG. 2, in particular, the first inflatable structural element 110 may comprise a second radially inner wall 116 which is transparent to the light such that light can be provided to the user 102 through the second wall. The light emitter 120 may be on the internal surface 115 of the first radially outer wall 114 or integrally formed with the first wall 114.

In this way, the light emitter 120 is spaced from the user 102. Accordingly, the amount of heat from the light emitter 120 reaching the user 102 may not be excessive, such that heat generated by the light emitter 120 may not cause discomfort for the user 102.

As is evident from FIGS. 2 and 3, the first wall 114 may face the second wall 116. This can enable light to travel efficiently from the light emitter 120 to the skin of the user 102.

The first inflatable structural element 110 may further comprise reflectors and/or diffusers for reflecting and/or diffusing the light such that the light so reflected and/or diffused can be provided to the user through the second wall 116. For example, as illustrated in FIG. 2, the first inflatable structural element 110 may comprise a third wall 118 which is reflective such that light may travel from the light emitter 120 to the user through the second wall 116 after being reflected off of the third wall 118. In this way more light may travel from the light emitter 120 to the user 102, such that the device 100 may have a greater luminous efficiency. In another example, the second wall 116 of the first inflatable structural element 110 may be diffusive, such that where a plurality of discrete light emitters 120 are provided a more even distribution of light may result on the skin of the user 102. Providing a more even distribution of light on the skin of the user 102 can provide an even treatment of the skin of the user 102, such an even treatment may be desired in particular treatment regimes.

Of course, any element of the at least one inflatable structural element, may comprise such reflectors and/or diffusers, for example, the further inflatable structural element 130 may additionally or alternatively comprise such reflectors and/or diffusers.

The body illumination device 100 may further comprise an air pump 158 for inflating the at least one inflatable structural element. Such an air pump 158 can enable easy inflation of the at least one inflatable structural element. If the body illumination device 100 is not provided with a pump 158, then the at least one inflatable structural element may be inflated by any other means, for example the inflatable element may be provided with a valve for connection to an external supply of air.

The at least one inflatable structural element may comprise an exhaust arranged to cool the user in use. For example, the at least one inflatable structural element may comprise at least one small hole which faces the user 102 in use. If the body illumination device 100 comprises an air pump 158, in use air may be pumped into the at least one inflatable structural element and then may exit the exhaust passing over the skin of the user 102. Such air flow may cool the skin of the user 102 (provided the air is cooler than the skin of the user). This can help to mitigate any heating effect caused by the light emitter 120. Accordingly, any heating effect of the light emitter 120 may at least partially reduced in order to provide a more comfortable experience for the user 102.

The light emitter 120 may comprise a solid state lighting element. In particular, the light emitter may comprise a light emitting diode (LED).

If the light emitter 120 comprises a solid state lighting element, the solid state lighting element may be integrally formed with the first wall 114 of the first inflatable structural element 110.

For example, the light emitter 120 may be integrally formed with the first wall 114 using smart textile technology (sometimes called E-textile, electronic textile or smart fabric technology). Smart textile technology enables the formation of textiles with integrated electronic components such as solid state lighting elements, for example LEDs.

This can enable the first wall 114 of the first inflatable structural element 110 to be provided with a very even profile. Accordingly, the body illumination device 100 can also be provided with a smooth profile when the at least one inflatable structural element is deflated, that is when the device 100 is in its storage or mounting configuration.

As illustrated in FIGS. 1 and 2, in particular, the body illumination device 100 may further comprise a control box 150. The body illumination device 100 may further comprise a controller 152 which may be mounted in the control box 150. The controller 152 may comprise a user interface 154 and driver circuitry for driving the light emitter 120. Alternatively, if the controller 152 does not comprise a user interface 154, the controller 152 may interface with the user through the use of another device, for example a wirelessly connected mobile computing device, such as a mobile phone. The air pump 158 mentioned above may also be located within the control box 150.

The controller 152 may be programmed or programmable with treatment regimes for various conditions. For example, a regime may include the intensity of treatment light, the wavelength of treatment light and/or the duration of treatment.

Figure 4:
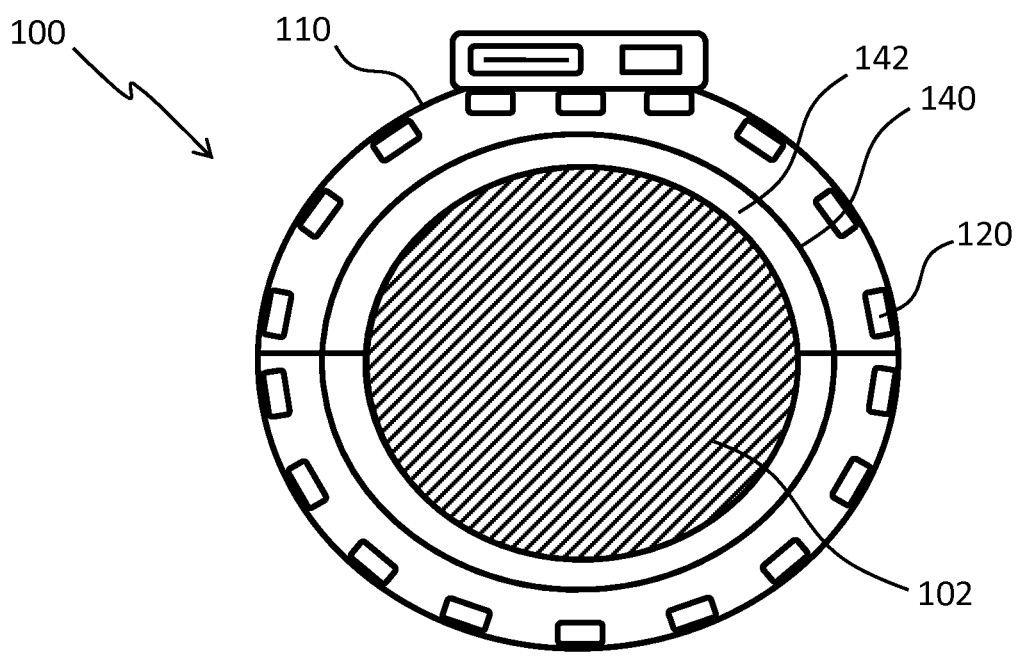
FIG. 4 shows a schematic cross-sectional view of another body illumination device.

FIG. 4 illustrates another embodiment of a body illumination device 100, this body illumination device 100 is similar to the device 100 illustrated in FIGS. 1 to 3, accordingly, only the differences will be described and like reference numerals are used.

As shown in FIG. 4, the at least one inflatable structural element may further comprise a second inflatable structural element 140 for providing a thermal cushion between the user 102 and the light emitter 120. The second inflatable structural element 140 is at least partially transparent to the light. Preferably, the second inflatable structural element 140 is at least mostly transparent to wavelengths of the treatment light which is most beneficial to the skin condition which it is desired to treat.

There is thus an outer set of inflatable compartments which include the light emitter and an inner set of inflatable compartments.

Accordingly, the amount of heat from the light emitter 120 reaching the user 102 may be reduced in comparison with the body illumination device described above and illustrated in FIGS. 1 to 3, and an even more comfortable experience may be provided for the user 102. Such a second inflatable structural element 140 may be particularly advantageous where the light emitter 120 provides a high luminous output, as light emitters which provide a high luminous output may also provide a high heat output.

Alternatively, the second inflatable structural element 140 may not be inflated in use, this means that the light emitter 120 is closer to the skin of the user in use 102 and may provide a more intense treatment when desired, although the thermal cushion may not be provided in this case. Accordingly, the device 100 may be suitable for a greater variety of body illumination regimes.

The second inflatable structural element 140 may further comprise reflectors and/or diffusers for reflecting and/or diffusing the light to provide a greater luminous efficiency and a more even distribution of light on the skin of the user 102.

The first (outer) inflatable element may be inflated prior to mounting the device on the arm or leg. When the device is positioned at the desired location, the second inflatable element may be inflated to fixate the device. This procedure can make the mounting/positioning process more comfortable.

The second inflatable structural element 140 may be in fluid communication with the first inflatable structural element 110 such that inflation of one inflatable structural element causes inflation of the other. Of course, such fluid communication must not be so great as to completely mitigate the thermal cushion provided by the second inflatable structural element 140. Alternatively, the second inflatable structural element 140 may be provided with its own individual air supply, e.g. its own connection to pump 158, its own pump, or its own valve for connection to an external air supply.

If the body illumination device 100 comprises an exhaust arranged to cool the user in use, as described above, the second inflatable structural element 140 may comprise the exhaust. This can also provide the above-mentioned advantages of cooling the user 102 in use, and can therefore provide a particularly comfortable experience for the user 102.

FIGS. 5 to 8 illustrate another embodiment of a body illumination device 100, this body illumination device 100 is similar to the devices 100 described above and illustrated in FIGS. 1 to 4 but on a larger scale, accordingly, only the differences will be described in detail and like reference numerals are used.

Figure 6:
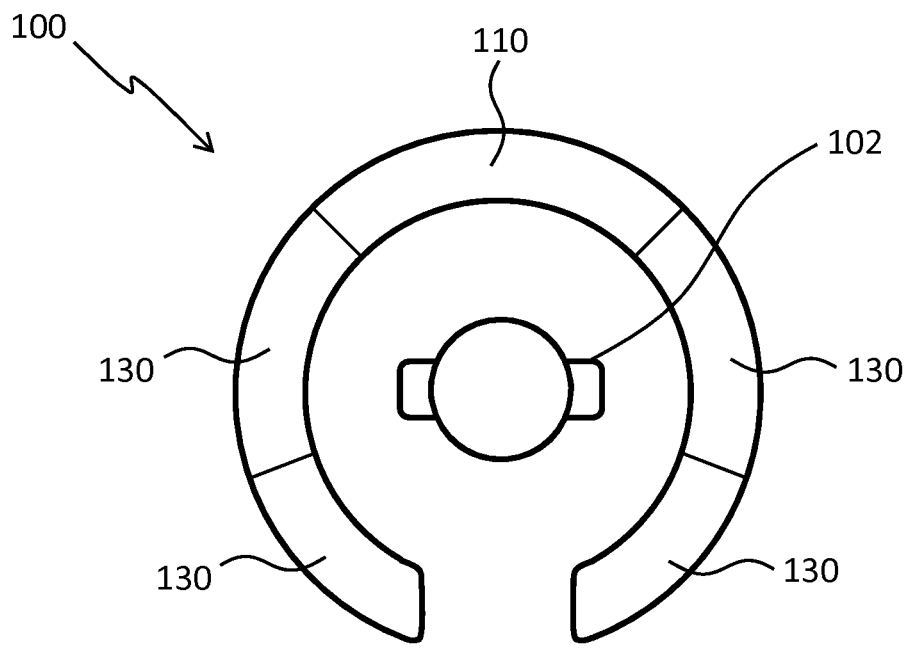
FIG. 6 shows a schematic plan view of the body illumination device of FIG. 5.

The body illumination device 100 is adapted to surround the user 102. In particular, as illustrated in FIG. 6, the body illumination device 100 is adapted to provide a whole body treatment to the user 102 and the body illumination device 100 may form a cabin into which the user 102 can walk.

This body illumination device 100 in this example has a principle advantage that the device 100 may be stored easily, the device 100 may not require expensive structural components (such that the body illumination device may be provided in a cost-effective manner) and the device 100 may be easy to use.

Further, prior art light therapy cabins are particularly bulky, heavy and expensive devices that take up a lot of floor space even when not in use, therefore the device 100 illustrated in FIGS. 5 to 8 may be particularly easy to store when compared with such prior art light therapy cabins. Additionally, prior art light therapy cabins require considerable expense to install, this means that home use of prior art light therapy cabins is not particularly feasible. However, home use of the device 100, given its ease of installation, relatively light weight and other advantages discussed above, may be particularly feasible. Yet further, the body illumination device 100 may be stored in a relatively compact state by deflating the at least one inflatable structural element.

The at least one inflatable structural element in this case typically comprises a set of inflatable structural elements comprising the first structural element 110 and further structural elements 130. As discussed above, the further inflatable structural elements 130 may be similar or identical to the first inflatable structural element 110.

Figure 5:
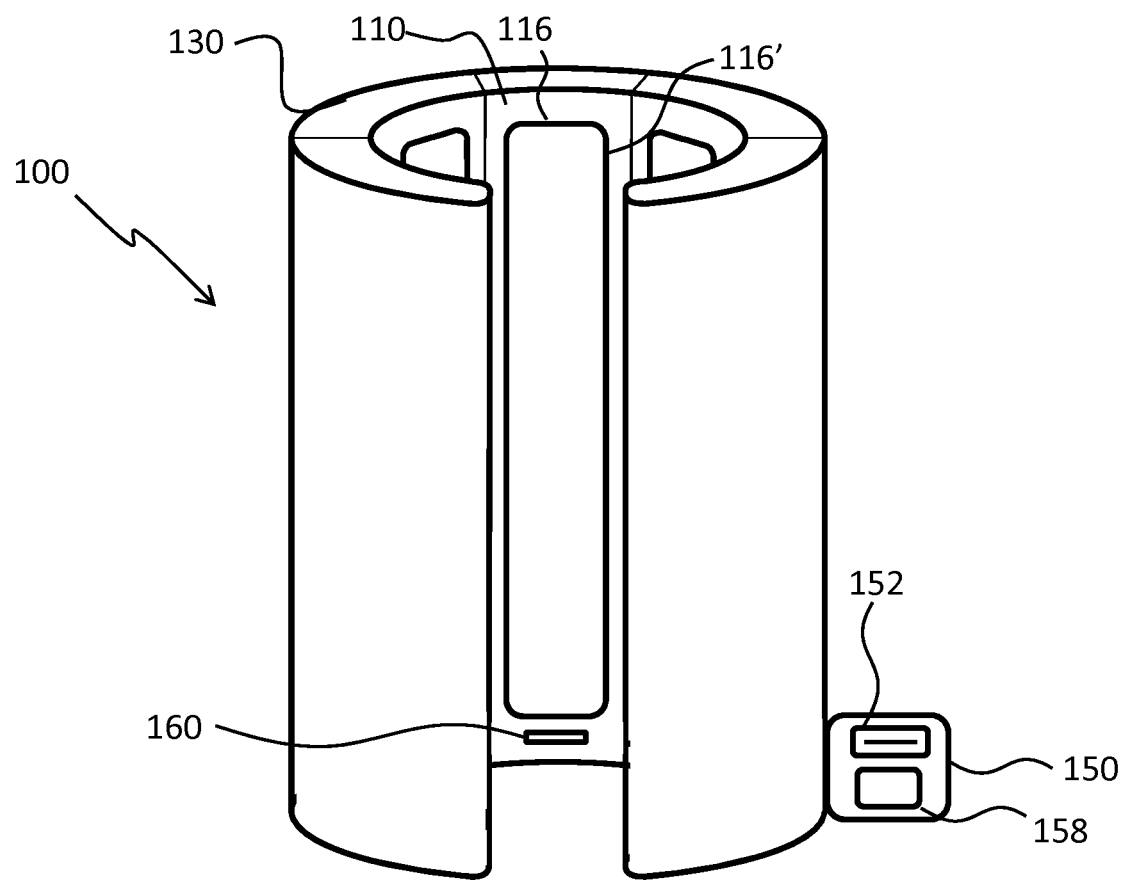
FIG. 5 shows a schematic perspective view of another body illumination device.
Figure 7:
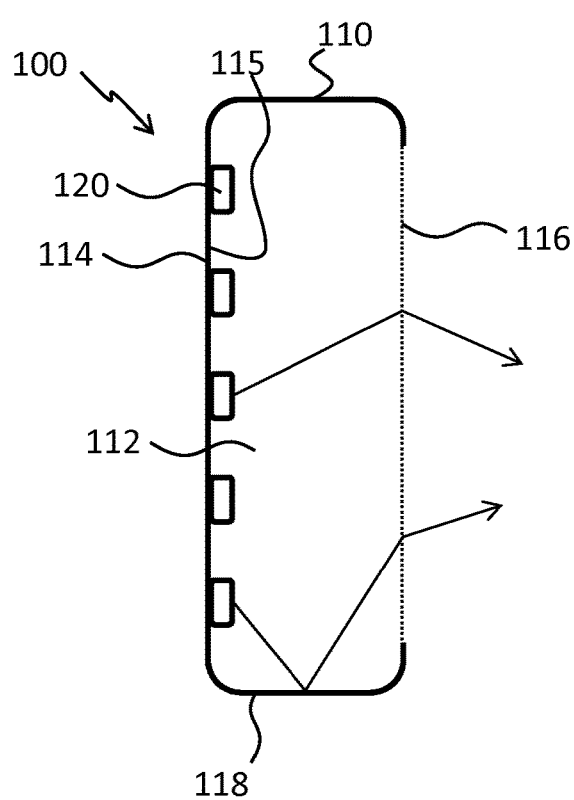
FIG. 7 shows a schematic cross-sectional view of the body illumination device of FIG. 5.

With reference to FIG. 7, in particular, and in a similar way to that discussed above, the first inflatable structural element 110 may comprise a second wall 116 which is transparent to the light such that light can be provided to the user 102 through the second wall 116. The light emitter 120 may also be on the internal surface 115 of the first wall 114 or integrally formed with the first wall 114. As discussed above this means that the light emitter 120 is spaced from the user 102. Accordingly, the amount of heat from the light emitter 120 reaching the user 102 may not be excessive and therefore may not cause discomfort for the user 102 in use. The light emitter may instead be on the inside wall as shown in FIG. 5, particularly as the inner wall of the cabin is spaced from the user. The cabin is self-supporting on the ground rather than fixing to the user as in the previous examples.

As is evident from FIG. 7, the first wall 114 may face the second wall 116. This can enable light to travel efficiently from the light emitter 120 to the skin of the user 102.

The first inflatable structural element 110 may further comprise reflectors and/or diffusers for reflecting and/or diffusing the light such that the light so reflected and/or diffused can be provided to the user through the second wall 116. For example, as illustrated in FIG. 7, the first inflatable structural element 110 may comprise a third wall 118 which is reflective such that light may travel from the light emitter 120 to the user through the second wall 116 after being reflected off of the third wall 118. In another example, the second wall 116 of the first inflatable structural element 110 may be diffusive, such that where a plurality of discrete light emitters 120 are provided a more even distribution of light may result on the skin of the user 102. As discussed above, these features can provide a greater luminous efficiency and/or a more even distribution of light on the skin of the user 102.

Of course any element of the at least one inflatable structural element, may comprise such reflectors and/or diffusers, for example, the further inflatable structural elements 130 may additionally or alternatively comprise such reflectors and/or diffusers.

Figure 8:
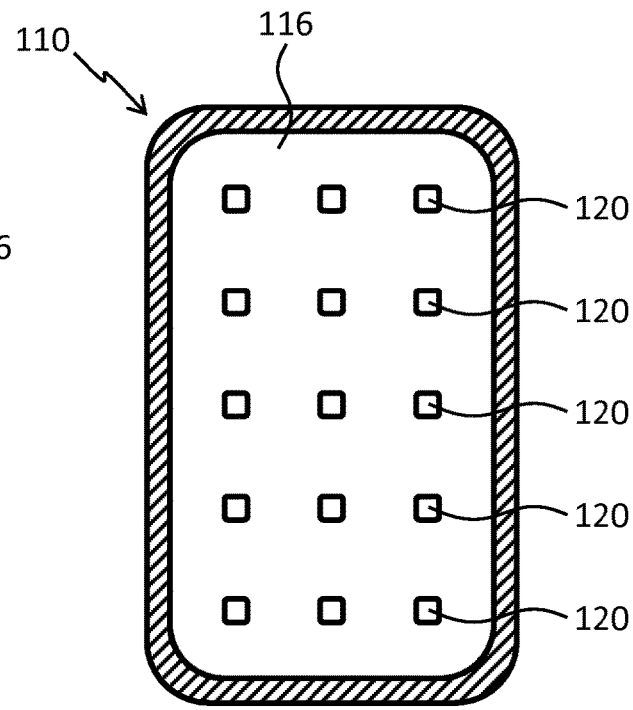
FIG. 8 shows an enlarged schematic view of the body illumination device of FIG. 5.

FIG. 8 illustrates an alternative view of part of the first inflatable structural element 110 from the point of view of the user 102 from within the body illumination device 100. The first inflatable structural element 110 is illustrated as having a second wall 116. The second wall 116 is transparent or includes a transparent window (shown as 116' in FIG. 5) and the light emitter 120 on the first wall 114 is visible through the second wall 116.

The body illumination device 100 may again further comprise an air pump 158 for inflating the at least one inflatable structural element. An air pump 158 may be particularly advantageous where the body illumination device 100 is adapted to surround the user, as such a device 100 may comprise relatively large inflatable structural elements. Clearly, the benefit gained by providing an air pump 158 may be greater for devices 100 comprising larger inflatable structural elements.

As shown in FIG. 5, the at least one inflatable structural element may comprise an exhaust 160 arranged to cool the user in use. As described above, the at least one inflatable structural element may comprise at least one small hole 160 which faces the user 102 in use. If the body illumination device 100 comprises an air pump 158, in use air may be pumped into the at least one inflatable structural element and then may exit the exhaust passing over the skin of the user 102. As also described above, such air flow may cool the skin of the user 102 and may therefore provide a more comfortable body illumination device 100 in use.

The light emitter 120 may be as described above. In particular, the light emitter may comprise a solid state lighting element, for example, a light emitting diode (LED) and the solid state lighting element may be integrally formed with the first wall 114 of the first inflatable structural element 110 (for example using smart textile technology). This can provide the advantages mentioned above.

As discussed above, the device 100 of FIGS. 5 to 8 may also comprise a similar controller 152 to that described above.

In a like manner to that discussed above with reference to FIG. 4, the at least one inflatable structural element of the device 100 illustrated in FIGS. 5 to 8 may further comprise a second inflatable structural element for providing a thermal cushion between the user 102 and the light emitter 120.

Figure 9:
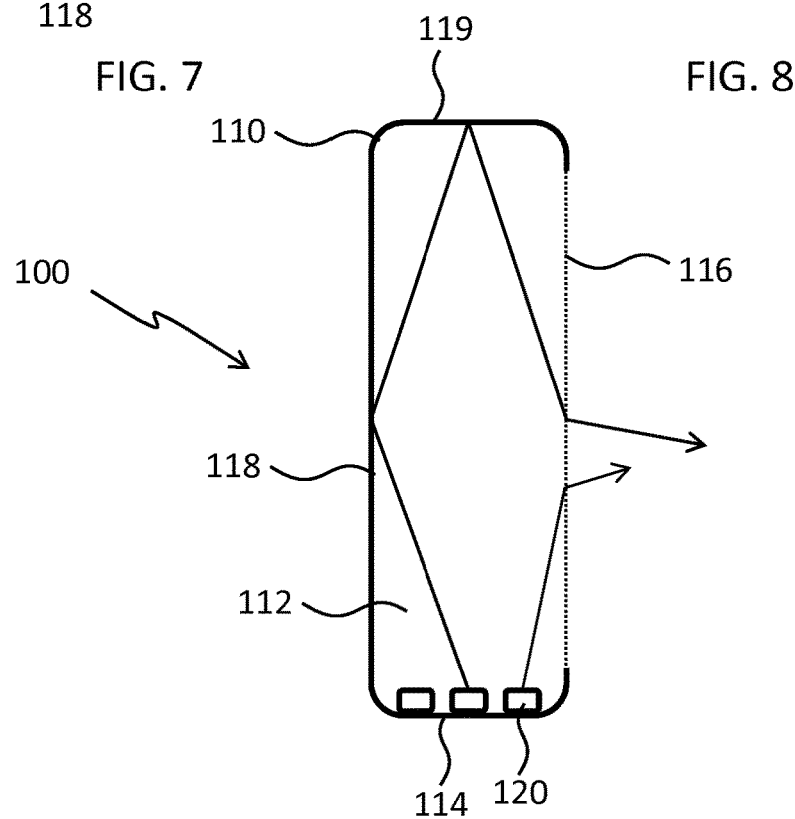
FIG. 9 shows a schematic cross-section sectional view of another body illumination device.

FIG. 9 illustrates an alternative embodiment of a body illumination device, the body illumination device 100 is similar to that described with reference to FIGS. 5 to 8, accordingly, only the differences will be described and like reference numerals are used. In this embodiment, the first wall 114 of the first inflatable structural element 110 (i.e. the one that includes the light emitter) is in the base of the body illumination device 100.

As mentioned above, the first inflatable structural element 110 may further comprise reflectors and/or diffusers for reflecting and/or diffusing the light such that the light so reflected and/or diffused can be provided to the user through the second wall 116.

For example, as illustrated in FIG. 9, the first inflatable structural element 110 may comprise a third (rear) wall 118 and/or a fourth (top) wall 119 which is reflective such that light may travel from the light emitter 120 to the user through the second wall 116 after being reflected off of the third and/or fourth wall 118, 119. In another example, the second wall 116 of the first inflatable structural element 110 may be diffusive, such that where a plurality of discrete light emitters 120 are provided a more even distribution of light may result on the skin of the user 102. As discussed above, these features can provide a greater luminous efficiency and a more even distribution of light on the skin of the user 102.

Further, as illustrated, this can enable the light emitter 120 to be provided in the base of the first inflatable structural element 110. Such an arrangement may be advantageous as it may not be necessary for the first inflatable structural element 110 to support the weight of the light emitter 120, if the light emitter 120 is provided in the base of the first inflatable structural element 110, as the base of the first inflatable structural element may rest on the ground in use. Furthermore, the electric wiring for the lighting is contained in a smaller area at the base, which is a more cost effective design. The lighting can then be provided on a rigid printed circuit board, so that one wall of the inflatable chamber is then rigid.

Of course any element of the at least one inflatable structural element, may comprise such reflectors and/or diffusers, for example, the further inflatable structural elements 130 may additionally or alternatively comprise such reflectors and/or diffusers.

With respect to all of the above described embodiments, the light output of the light emitter 120 is typically in the wavelength range of from 280 nm to 1400 nm with intensities up to 100 mW/cm$^2$. The light emitter may emit UVB (280 nm to 315 nm), UVA (315 nm to 380 nm or 315 nm to 400 nm), visible (380 nm to 780 nm or 400 nm to 780 nm), in particular blue light (450 nm to 495 nm), and/or IR-A (780 nm to 1400 nm) light, depending on the condition to be treated. The light emitter may emit in the long-wave part of the UVB spectrum (e.g. between 300 and 320 nm or 305 nm and 315 nm). A range of particular interest is 400 nm to 650 nm. For example, for use to treat psoriasis.

The walls 114, 134 of the at least one inflatable structural element may be made of any suitable material, such as polyvinyl chloride (PVC), textile-reinforced urethane plastic and/or rubber.

The body illumination devices 100 described above are for use in a method of treatment comprising the steps of:
surrounding at least a part of a user,
inflating at least one inflatable structural element 110,
providing power to a light emitter 120, and
providing treatment light to the user 102.

The treatment may be of, psoriasis, eczema or skin cancer, in particular, or of any other condition, for example a skin condition, which may be treated by providing treatment light to a user 102.

The method comprises inflating the at least one inflatable structural element and providing treatment light to the user 102 using the body illumination device 100.

It will be understood from the examples above that the inflatable part may comprise a single compartment or multiple compartments according to the size and required rigidity. Similarly, the light emitter can be arranged on or in any surface, providing there is a path to the patient, which may include reflections and/or transmission through a scattering medium.

Other variations to the disclosed embodiments can be understood and effected by those skilled in the art in practicing the claimed invention, from a study of the drawings, the disclosure, and the appended claims. In the claims, the word "comprising" does not exclude other elements or steps, the indefinite article "a" or "an" does not exclude a plurality, and the word "first" before an element or step does not imply the presence or absence of a "second" or further such element(s) or step(s). The mere fact that certain measures are recited in mutually different dependent claims does not indicate that a combination of these measured cannot be used to advantage. Any reference signs in the claims should not be construed as limiting the scope.

The invention claimed is:

1. A body illumination device adapted to surround at least a part of a user comprising:
    at least one inflatable structural element configured to hold air when inflated and including a first inflatable structural element comprising:
    a first inflatable chamber comprising a first wall formed from an electrically conductive textile;
    a light emitter on or integrally formed with an internal surface of the textile of said first wall for providing light to the user, and
    a second wall which is transparent to the light emitted by the light emitter such that light is provided to the user from the light emitter through the second wall.

2. The body illumination device according to claim 1, wherein the first wall faces the second wall and the second wall includes transparent windows spaced along the second wall, wherein the windows are separated by non-transparent portions.

3. The body illumination device according to claim 2, wherein the body illumination device is adapted to encircle at least one of a limb, the torso, the neck and the head of the user, wherein the light emitter is a plurality of light emitters radially directed inward along an entire extension of the first wall.

4. The body illumination device according to claim 3, wherein in use the limb, the torso, the neck or the head is surrounded by the at least one inflatable structural element thereby to fix the device to the limb, torso, neck or head by inflation of the at least one inflatable structural element when inflated.

5. The body illumination device according to claim 2, wherein the body illumination device is adapted to surround the user by forming a cabin into which the user can walk, wherein the at least one inflatable structural element comprises an exhaust formed as a hole through the second wall and arranged to cool the user in use from air present in the first inflatable structural element.

6. The body illumination device according to claim 1, wherein the first inflatable structural element further comprises reflectors and/or diffusers radially extending inward for reflecting and/or diffusing the light such that the light so reflected and/or diffused is provided to the user through the second wall, wherein the light emitter is attached to the radial extension.

7. The body illumination device according to claim 1, further comprising an air pump configured to inflate the at least one inflatable structural element.

8. The body illumination device according to claim 1, wherein the at least one inflatable structural element comprises an exhaust formed as a hole through the second wall and arranged to cool the user in use from air present in the first inflatable structural element.

9. The body illumination device according to claim 1, wherein the light emitter comprises a solid state lighting element.

10. The body illumination device according to claim 9, wherein the light emitter is integrally formed with the first wall of the first inflatable structural element and the textile is textile-reinforced urethane.

11. The body illumination device according to claim 1, wherein the at least one inflatable structural element further comprises a second inflatable structural element configured to provide a thermal cushion between the user and the light emitter and wherein the second inflatable structural element is at least partially transparent to the light and is configured to diffuse light passing therethrough.

12. The body illumination device according to claim 1, further comprising a controller which comprises a user interface and driver circuitry configured to drive the light emitter and the controller is mounted to an outer surface of the textile of the first wall.

13. The body illumination device according to claim 1, wherein the first inflatable structural element further comprises reflectors radially extending inward for a portion and thereafter circumferentially extending to form a window in the second wall for reflecting the light such that the reflected light is provided to the user through the window.

14. The use of a body illumination device according to claim 1, in a method of treatment comprising acts of:
    surrounding at least a part of a user,
    inflating at least one inflatable structural element,
    providing power to a light emitter,
    providing treatment light to the user, and
    cooling the user through a hole that extends through the second wall from air present in the first inflatable structural element.

15. The use of a body illumination device according to claim 14, wherein the treatment is provided to sufferers of psoriasis, eczema, or skin cancer.

* * * * *